United States Patent
Ashe et al.

(10) Patent No.: US 9,854,994 B2
(45) Date of Patent: Jan. 2, 2018

(54) METHOD AND SYSTEM FOR WIRELESS RESPIRATION RATE MONITORING USING SPACE AND FREQUENCY DIVERSITIES

(71) Applicant: General Electric Company, Schenectady, NY (US)

(72) Inventors: Jeffrey Michael Ashe, Gloversville, NY (US); Ting Yu, Niskayuna, NY (US); Yang Zhao, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 273 days.

(21) Appl. No.: 14/716,522

(22) Filed: May 19, 2015

(65) Prior Publication Data

US 2016/0338617 A1    Nov. 24, 2016

(51) Int. Cl.
*A61B 5/08* (2006.01)
*A61B 5/00* (2006.01)

(52) U.S. Cl.
CPC .......... *A61B 5/0816* (2013.01); *A61B 5/7278* (2013.01); *A61B 5/7282* (2013.01); *A61B 5/742* (2013.01); *A61B 5/7405* (2013.01); *A61B 5/746* (2013.01)

(58) Field of Classification Search
CPC .......................... A61B 5/7282; A61B 5/0816
See application file for complete search history.

(56) References Cited

U.S. PATENT DOCUMENTS

| | | | |
|---|---|---|---|
| 8,740,793 B2 | 6/2014 | Cuddihy et al. | |
| 2009/0203972 A1* | 8/2009 | Heneghan | A61B 5/0507 600/301 |
| 2013/0053653 A1* | 2/2013 | Cuddihy | A61B 5/0205 600/301 |

FOREIGN PATENT DOCUMENTS

WO    2013/025922 A1    2/2013

* cited by examiner

*Primary Examiner* — Christian Jang
(74) *Attorney, Agent, or Firm* — GE Global Patent Operation

(57) ABSTRACT

A system and method include a plurality of sensors proximate a subject, wherein each sensor includes a plurality of antennas, and wherein each sensor operates on a plurality of frequency channels. The method includes receiving, at a respiration module, a signal associated with each antenna for each of the plurality of frequency channels; and calculating a respiration rate of the subject based on the received signal associated with each antenna for each of the plurality of frequency channels. Numerous other aspects are provided.

28 Claims, 4 Drawing Sheets

_METHOD AND SYSTEM FOR WIRELESS RESPIRATION RATE MONITORING USING SPACE AND FREQUENCY DIVERSITIES_

FIELD

One or more embodiments described below relate to the health monitoring, and more particularly to wireless based methods and systems for monitoring the respiration of a person.

BACKGROUND

It is often desirable to monitor the respiration rate of a person as an indication of a health state of a person, and in particular in a non-contact way. While the respiration rate of the person is monitored, the person may change their location and posture, which may impact the detected monitored respiration rate.

Systems and methods are desired which provide a more accurate non-invasive respiration rate monitoring.

SUMMARY

In accordance with an embodiment of the invention, a method is provided. The method includes providing a plurality of sensors proximate a subject, wherein each sensor includes a plurality of antennas, and wherein each sensor operates on a plurality of frequency channels; receiving, at a respiration module, a signal associated with each antenna for each of the plurality of frequency channels; and calculating a respiration rate of the subject based on the received signal associated with each antenna for each of the plurality of frequency channels.

In accordance with another embodiment of the invention, a system is provided. The system includes a plurality of sensors, positioned proximate a subject, wherein each sensor includes a plurality of antennas, and wherein each sensor operates on a plurality of frequency channels; a respiration module operative to: receive a signal associated with each antenna for each of the plurality of frequency channels; and calculate a respiration rate of the subject based on the received signal associated with each antenna for each of the plurality of frequency channels.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of elements for carrying out one or more of the method steps described herein; the elements can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Other features and aspects of the present invention will become more fully apparent from the following detailed description, the appended claims and the accompanying drawings.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

It is often desirable to monitor the respiration rate of a person as an indication of a health state of a person, and in particular in a non-contact way. While the respiration rate of the person is monitored, the person may change their location and posture, which may impact the detected monitored respiration rate. For example, conventional respiration monitors that use a single antenna on each sensor may assume the location and posture of the person is known beforehand, e.g., lying on a bed, so that the respiration rate may be estimated by pointing the antenna(s) at the chest/abdominal region of the person. However, people will not stay at the same location and keep the same posture all the time. Thus if the location of the person is unknown, or if the person changes their posture, performance of the single antenna system will degrade.

In one or more embodiments, space diversity may include the use of 1) multiple sensors and 2) multiple antennas. For example, in one or more embodiments, the minimum number of sensors used may be two. For a two-sensor system, multiple antennas may be placed on each sensor, so that the system is robust to different postures and locations.

Accordingly, a system and method to provide a more accurate respiration rate is provided. A technical effect of embodiments of the invention is the provision of a more accurate respiration rate that may be determined in a low-cost and easy to use manner. Embodiments of the invention may use low-cost commercial off the shelf wireless communication units (e.g., sensors) as opposed to sophisticated sensing hardware, or may use any other suitable sensing hardware. Another technical effect of embodiments of the invention is that the systems and methods may be applied to different wireless communication systems and protocols. For example, embodiments of the invention may be applied to devices with IEEE 802.15.4 protocol and/or may be used in WiFi communication systems per IEEE 802.11n protocol.

As used herein, "non-intrusive," "non-invasive," and "contact-less" monitoring are used interchangeably to refer to observing and/or measuring one or more parameters associated with a person with no, or negligible, direct physical contact with the person. As used herein, "space diversity" may refer to sensor nodes with multiple antennas deployed at different locations. As used herein, "frequency diversity" may refer to radio nodes communicating on multiple frequency channels. As used herein "patient" and "subject" may be used interchangeably.

Figure 1:
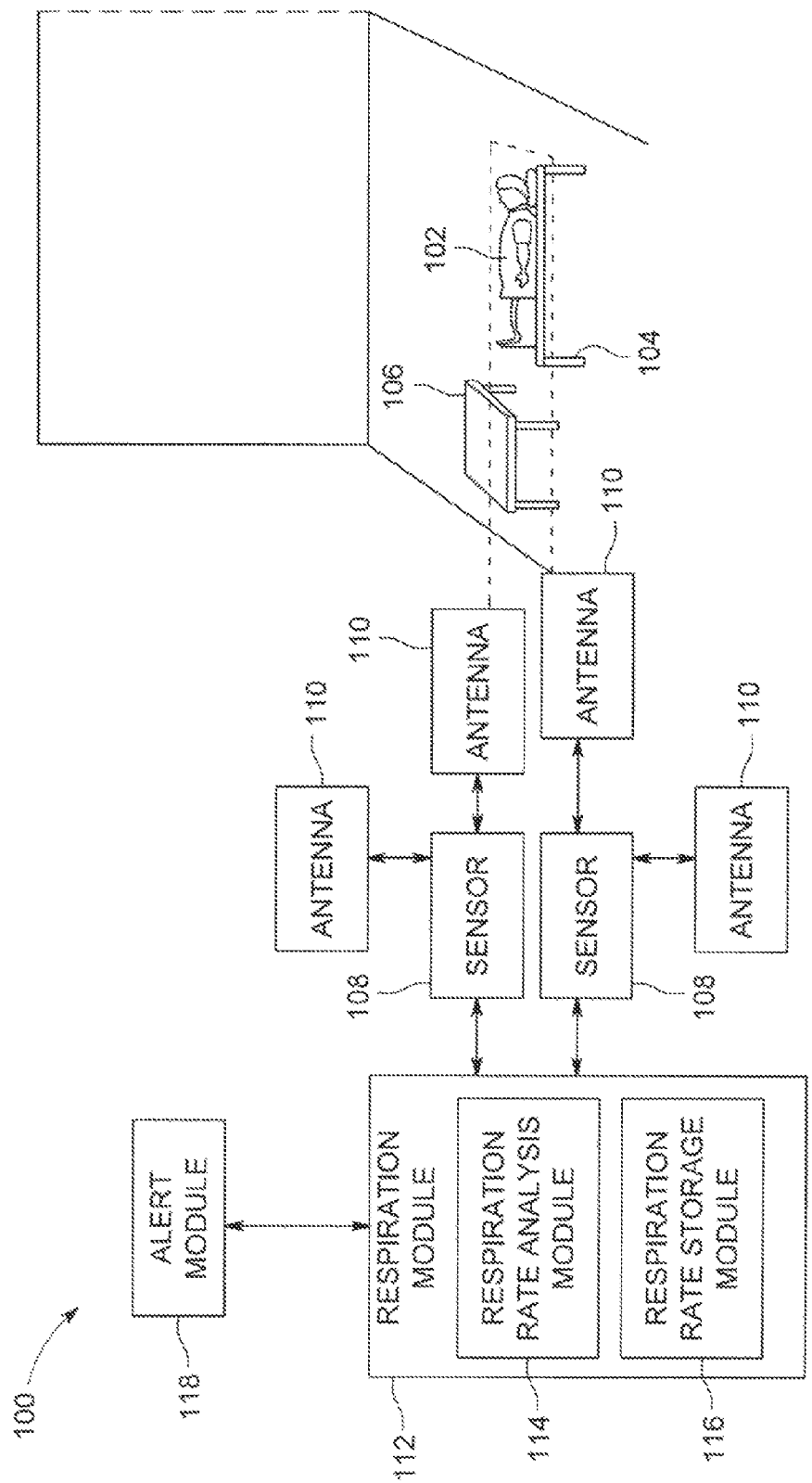
FIG. 1 illustrates a block diagram of system architecture according to some embodiments.

FIG. 1 is a block diagram of an example of a respiration rate monitoring system 100 for contact-less monitoring of a patient 102, such as a person or an animal. The patient 102 may be monitored by the system 100 in any suitable space (e.g., room; hospital room, etc.) to assess a respiration rate of the patient 102. While the patient 102 is shown laying in a bed 104 herein, the patient 102 may be in any other suitable location (e.g., mobile in the room, sitting in a chair, reclining in a chair, etc.) The space may include one or more objects 106, such as chairs, beds, tables, columns, etc. In certain scenarios, these objects 106 may obstruct the direct line-of-sight (LOS) between the system 100 and the patient 102.

The system 100 may include two or more sensors 108 for non-intrusively monitoring the patient 102. Each sensor 108 may include two or more antennas 110 coupled thereto. In one or more embodiments, directional antennas may be used to focus more radio energy on the patient 102, which may result in a signal that is more sensitive to patient motion. In one or more embodiments, any suitable antenna may be used (e.g., PCB antenna, directional antenna, etc.). Of note, the use of multiple sensors, each with multiple antennas deployed at different locations, herein referred to as "space diversity," may provide a more accurate estimated respiration rate. Each sensor 108 may include a transmitter-receiver pair (not shown). In one or more embodiments, the sensors may be wireless radio sensors, optical sensors, acoustic sensors, or any other suitable sensor. As shown herein, the sensors 108 are positioned proximate the foot of the bed 104, where the patient 102 is resting. Other suitable sensor configurations may be used (e.g., sensors may be attached to walls or embedded in beds, for example).

While monitoring the patient 102, the sensors 108 may transmit, via the antenna 110, signals towards the patient 102. Some signals may go around the patient, some signals may go through the patient, and some signals may be reflected by the patient. In one or more embodiments, the sensors 108 may receive, via the antenna 110, corresponding echo signals (e.g., pulse sequences) that are a combination of reflection, attenuation and scattering.

The system 100 may include a respiration module 112 operative to receive signals from the two or more sensors 108. In one or more embodiments, the respiration module 112 may include a respiration rate analysis module 114 and a respiration rate storage module 116. The respiration module 112 may determine the respiration rate of the patient 102 using the received signals, as described further below. In one or more embodiments, the respiration module 112 may, via the respiration rate analysis module 114, filter the received signals to extract respiration data into signal frames.

The system 100 may also include an alert module 118. In one or more embodiments, the alert module 118 may receive a signal from the respiration module 112 indicating the respiration rate calculated by the respiration module 112 is outside a corresponding threshold. In one or more embodiments, in response to receiving a signal indicating the calculated respiration rate is outside a corresponding threshold, the alert module 118 may generate at least one of an audio output (e.g., an alarm), a visual output (e.g., flashing lights, a display message), an alert message or combination thereof at the alert module 118 based on the calculated respiration rate being outside a corresponding threshold. In one or more embodiments, the alert module 118 may sound an alarm, send a voicemail, text message and/or email to a mobile device of appropriate personnel and/or to another monitoring system through a wired and/or wireless link.

Figure 2:
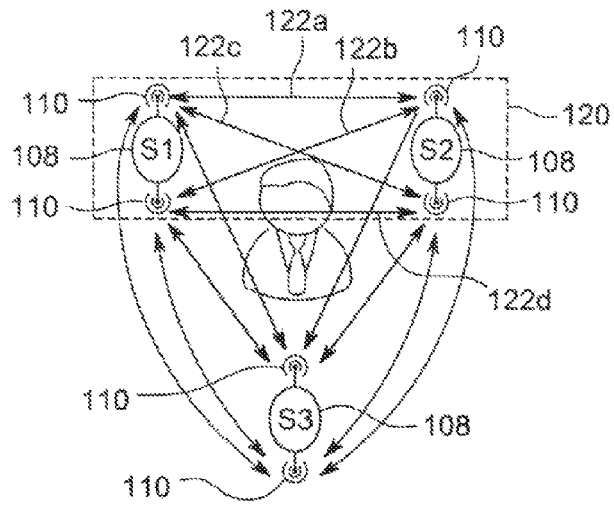
FIG. 2 illustrates a diagram of communication paths of a system according to some embodiments.

Turning to FIG. 2, a diagram of communication paths of an example of the respiration rate monitoring system 100 for contact-less monitoring of a patient 102 is shown. The same system 100 is used in FIG. 1 and FIG. 2, except the sensors 108 are placed in a different orientation. FIG. 2 includes three sensors 108, and each sensor 108 includes two antenna 110. For each pairwise link 120 (represented by dotted box) between two sensors 108, there may be four bi-directional links 122 among four antennas 110. As used herein, a "bi-directional link" may refer to a single physical two-way communication link between two antennas at two sensors. For example, for the pairwise link 120 between sensors 1 (S1) and 2 (S2), there may be bi-directional links 122a, 122b, 122c, and 122d. Bi-directional link 122a, for example, may include two communication links: one from antenna 1 at sensor 1 (S1) to antenna 1 at sensor 2 (S2), and one from antenna 1 at sensor 2 (S2) to antenna 1 at sensor 1 (S1) (the opposite direction). In general, for a static wireless sensor network with N sensors, if each sensor 108 has M antennas, then the number of links, L, may be represented by $L=N(N-1)M^2/2$ for bi-directional links. While bi-directional links are described herein, the formula may be applicable to directional links, which may include two physical one-way communication links between two antennas at two sensors. In other embodiments, the number of links, L, may be represented by $L=N(N-1)M^2$ for directional links.

As shown in FIG. 2, the line of sight (LOS) of link 122a does not pass through the body of the patient 102, but links 122b and 122a do. While link 122a may not be sensitive to motion of the patient, as it does not pass through the body of the patient, only one of 122b and 122c may be sensitive to the motion of the patient, even though both pass through the patient. The reason that only one may be sensitive may be due to the random nature of the multipath effect of the environment. In other words, the signal may pass through one or more objects, which may return/reflect signals of different strengths (including not reflecting a signal at all) and therefore instead of a single path, there may be multiple paths in which the signal is reflected back to the sensor. The multi-path signal may not be as sensitive as a single path signal. Since the received signal strength is the summation of all paths at the receiver, the reflected signal due to respiration motion may be buried in the signal that includes information that is not related to the respiration motion. Thus, it may be preferable to focus higher radio energy on the chest and abdominal area of a person, so that the LOS path may dominate the received signal.

Additionally, each sensor 108 may transmit and receive signals on multiple frequency channels ("frequency diversity"). Of note, for the same link 122 between a transmitter and receiver, different frequency channels may show different sensitivities to respiration motion. In one or more embodiments, combining measurements from multiple channels may increase the accuracy of the system. As such, in one or more embodiments, multiple frequency channels may be used for each bi-directional link 122. For example, with IEEE 802.15.4 protocol, there are 16 frequency channels: Channel 11 to Channel 26.

Figure 3:
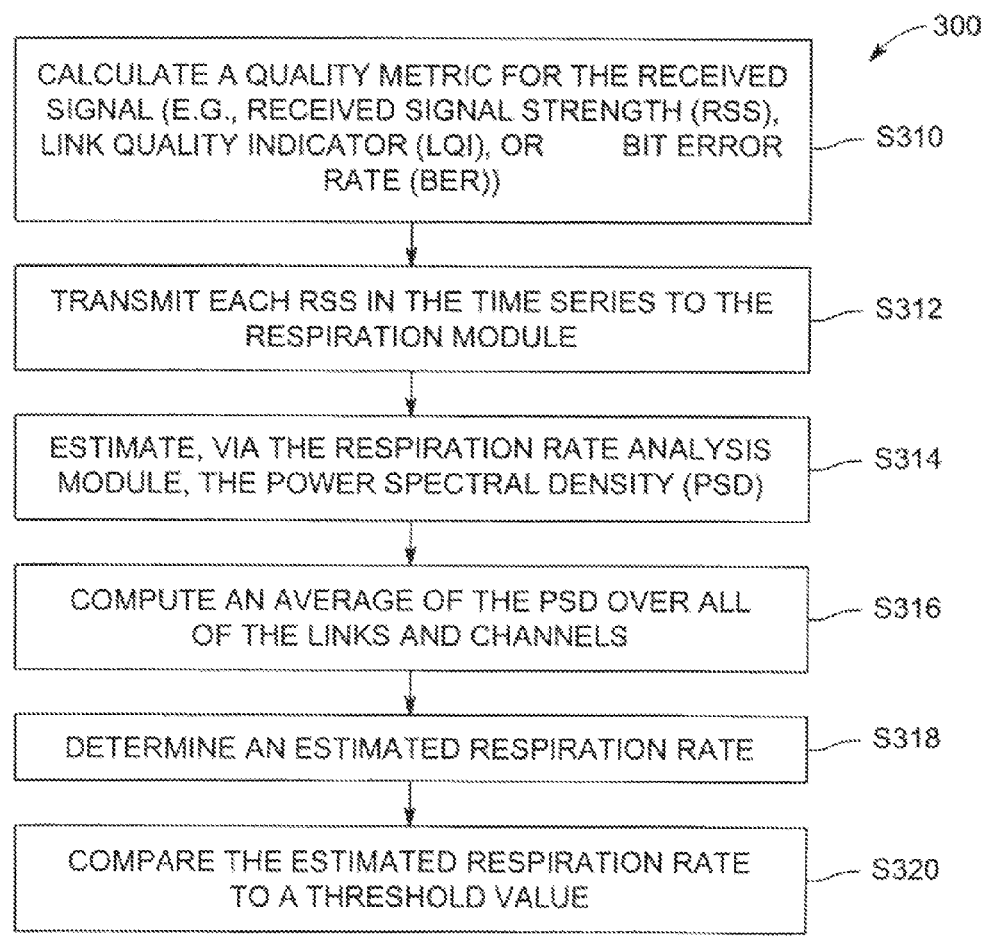
FIG. 3 is a flow diagram of a process according to some embodiments of the present invention.

FIG. 3 illustrates a method 300 that might be performed by all or some of the elements of the system 100 described with respect to FIGS. 1 and 2 according to some embodiments. The flow chart(s) described herein do not imply a fixed order to the steps, and embodiments of the present invention may be practiced in any order that is practicable. Note that any of the methods described herein may be performed using any suitable combination of hardware (e.g., circuit(s)), software or manual means. For example, a non-transitory computer-readable storage medium (e.g., a fixed disk, a floppy disk, a CD, a DVD, a Flash drive, or a magnetic tape) may store thereon instructions that when executed by a machine result in performance according to any of the embodiments described herein. In one or more embodiments, the components of the system 100 (e.g., the respiration module 112, the respiration rate analysis module 114, respiration rate storage module 116 and alert module 118) may be necessarily rooted in computer technology and may be conditioned to perform the process 300, such that the components and system 100 are special purpose elements configured to perform operations not performable by a general purpose computer or device. Examples of these processes will be described below with respect to the elements of the computing device, but embodiments are not limited thereto.

At S310, for each corresponding signal received 101 at the sensor 108, the sensor 108 calculates a quality metric for the received signal. While the example herein describes a received signal strength (RSS) as the quality metric, other quality metrics such as a link quality indicator (LQI) and Bit Error Rate (BER) may be used instead of RSS. In the non-limiting example used herein, at S310, the sensor 108 calculates a RSS for that signal during a user-defined period of time to create an RSSI time series. The calculated RSS may be at least partially indicative of breathing/respiration of the patient 102. In one or more embodiments, each sensor operates on multiple frequency channels, and a signal is measured for each bi-directional link 122, RSSI may be calculated for each of the multiple frequency channels operating on each antenna. Of note, calculating a quality metric for each of the multiple frequency channels operating on multiple antennas, may provide a higher granularity of quality metric which may result in a more robust and accurate respiration rate calculation. While embodiments herein describe a more accurate and robust respiration rate calculation using power spectral density (PSD) that accounts for the multiple frequency channels operating on multiple antennas, in other embodiments, the higher granularity provided by the multiple frequency channels operating on multiple antennas may be used to calculate the respiration rate via other processes. For example, the respiration rate analysis module 114 may calculate a respiration rate by detecting and then adding the number the peaks and troughs of the received signals in a chart (e.g., received RSS signals in FIG. 4), and dividing this sum by the time.

Figure 4:
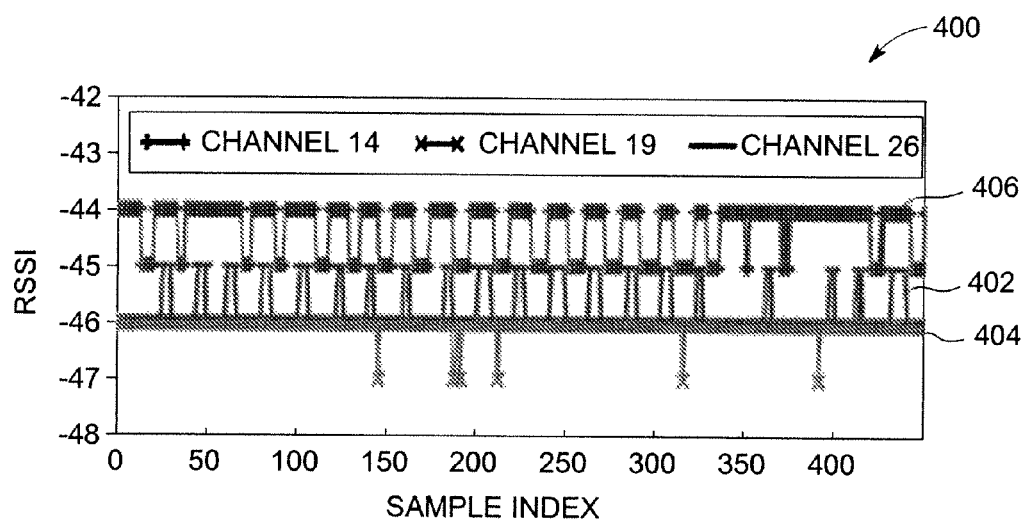
FIG. 4 is a graph of RSSI according to some embodiments of the present invention.

As described above, for IEEE 802.15.4 protocol, for example, there are 16 frequency channels: Channel 11 to Channel 26. As an example, RSSI from three frequency channels (Channel 14, 19 and 26) is shown in a chart 400 in FIG. 4. For a particular patient location and posture, not all measurements may be sensitive to the patient's respiration motion. For example, as shown in FIG. 4, the RSSI from 404 (Channel 19) is flatter and not as sensitive (e.g., less affected by chest motion) to respiration motion as the RSSI from 402 (Channel 14) and 406 (Channel 26) other two channels, which show period changes due to respiration motion. Of note, the combination of RSSI from multiple channels may improve the performance of the system, in particular as compared to single-channel systems.

At S312, the sensor 108 transmits 103 each RSSI in the time series to the respiration module 112. In one or more embodiments, the respiration module 112 may calculate a time series of RSS changes to capture periodic changes of RSS due to the respiration motion, for example. As used herein, "respiration motion" may be the human motion caused by respiration/breathing. The time series of RSS changes may be determined by determining an average RSS during a time window, and then subtracting the average RSS from each RSS signal in the time series.

At S314, the respiration rate analysis module 114 estimates the power spectral density (PSD) for the RSSI time series. The respiration rate analysis module 114 may use any suitable PSD estimator to estimate the PSD, such as a periodogram estimator (i.e., Fourier transform that uses a maximum likelihood estimation method), a Welch estimator, or Bartlett's method estimator, for example.

As used herein, for L communication links, each link operates on C frequency channels. Additionally, in one or more embodiments, the sampling rate of RSSI of a system may be much faster than a person's respiration rate. It may be assumed, in one or more embodiments, the respiration rate remains the same during the time when RSSI are measured from L links on C channels.

Figure 5:
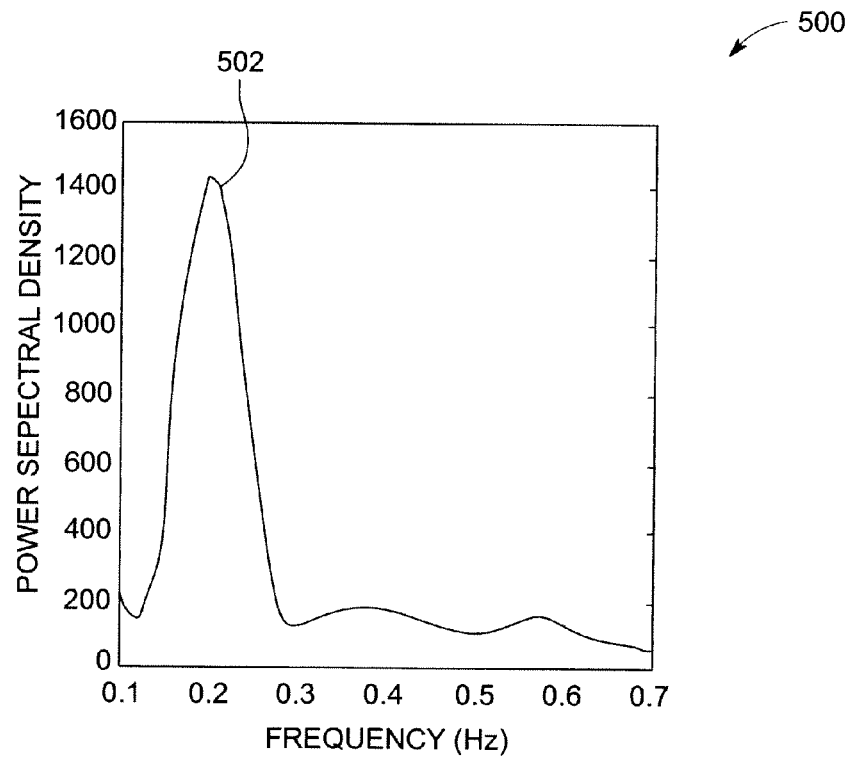
FIG. 5 is a graph of an estimated respiration rate according to some embodiments of the present invention.

Then in S316, the respiration rate analysis module 114 computes an average of the PSD over all of the links and channels (FIG. 5).

The respiration rate analysis module 114 then determines the respiration rate estimate in S318. To determine the respiration rate estimate, in one or more embodiments, the respiration rate analysis module 114 determines the maximum PSD value of the average PSD and calculates the frequency associated with the maximum PSD, via the following formula:

$$\hat{f} = \operatorname*{argmax}_{f_{min} \leq f \leq f_{max}} \sum_{l=1}^{L} \sum_{c=1}^{C} g(y_{c,l,T}) \quad (1)$$

where $\hat{f}$ is the estimate of respiration rate/frequency, arg max $f_{min} \leq f \leq f_{max}$ is the operator to find the maximum PSD value, L is the number of links, C is the number of frequency channels, $y_{c,l,T}$ is the time series of RSSI changes collected from link l on Channel c during a time period of length T, and g represents a particular PSD estimator.

For example, if the respiration rate estimator is a maximum likelihood estimation (MLE) estimator or method, the frequency formula (1) may be represented by the following formula:

$$\hat{f} = \operatorname*{argmax}_{f_{min} \leq f \leq f_{max}} \sum_{l=1}^{L} \sum_{c=1}^{C} \left| \sum_{t=i-T+1}^{i} y_{c,l,t} e^{-j2\pi f T_s t} \right|^2, \quad (2)$$

where i is the current time index, $j=\sqrt{-1}$, is the time window length (e.g., time period during which the RSSI time series is collected), and $T_s$ is the sampling period, and $|\sum_{t=i-T+1}^{i} y_{c,l,t} e^{-j2\pi f T_s t}|^2$ is the g in (1).

In one or more embodiments, the MLE estimator finds the estimate by using the value that maximizes the likelihood function.

In one or more embodiments, the respiration rate analysis module may provide a graph displaying the estimated respiration rate. For example, as shown in FIG. 5, a graph 500 of the average PSD over all the links and channels is provided, as described above with respect to S316. The peak location 502 (e.g., 0.2 Hz herein) is the estimate of the respiration rate.

Then at S320, the respiration rate analysis module 114 may compare the determined estimated respiration rate to a threshold value. In one or more embodiments, the threshold value may be user-defined. If the respiration rate analysis module 114 determines the estimated respiration rate is outside the threshold value, the respiration rate analysis module 114 may send a signal to the alert module 118 to generate an alert.

In one or more embodiments, the determined estimated respiration rate may be stored in the respiration rate storage module 116, where the stored rate may be used for future further analyses.

Figure 6:
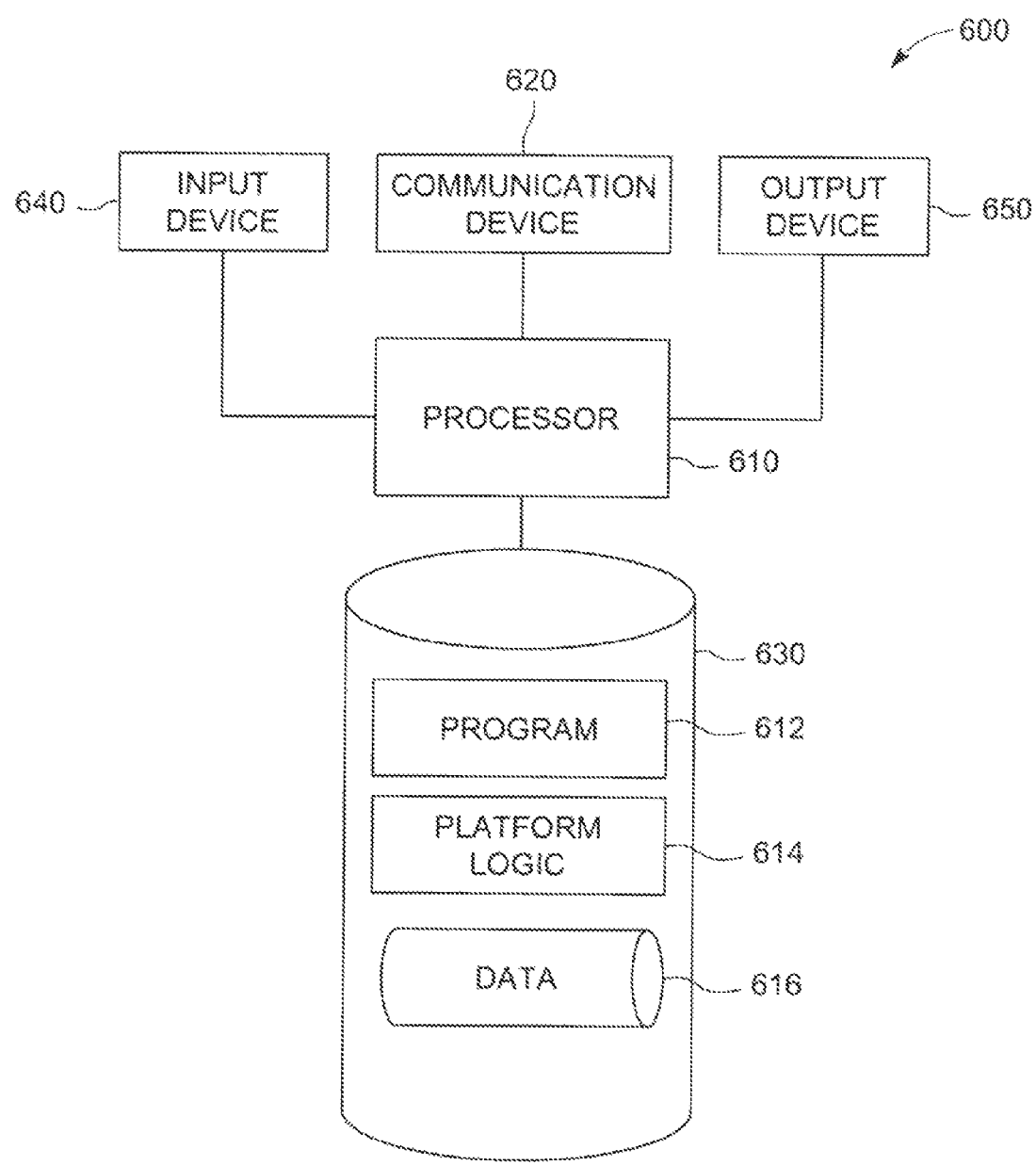
FIG. 6 is block diagram of a system according to some embodiments.

Note that the embodiments described herein may be implemented using any number of different hardware configurations. For example, FIG. 6 illustrates a Respiration Rate Platform 600 that may be, for example, associated with the system 100 of FIGS. 1 and 2. The Respiration Rate Platform 600 comprises a respiration rate processor 610, such as one or more commercially available Central Processing Units (CPUs) in the form of one-chip microprocessors, coupled to a communication device 620 configured to communicate via a communication network (not shown in FIG. 6). The communication device 620 may be used to communicate, for example, with one or more users or computers. The Respiration Rate Platform 600 further includes an input device 640 (e.g., a computer mouse and/or keyboard to enter information about transactions) and an output device 650 (e.g., a computer monitor or printer to output a transaction information report and/or evaluation).

The processor 610 also communicates with a storage device/memory 630. The storage device 630 may comprise any appropriate information storage device, including combinations of magnetic storage devices (e.g., a hard disk drive), optical storage devices, mobile telephones, and/or semiconductor memory devices. The storage device 630 stores a program 612 and/or respiration rate platform logic 614 for controlling the processor 610. The processor 610 performs instructions of the programs 612, 614, and thereby operates in accordance with any of the embodiments described herein. For example, the processor 610 may receive sensor data which may then be analyzed by the processor 610 to automatically determine a respiration rate of a patient. The storage device 630 may also store data 616 in a database, for example.

The process steps (e.g., programs 612, 614) stored in the storage device 630 may be read from one or more of a computer-readable medium, such as a floppy disk, a CD-ROM, a DVD-ROM, a Zip™ disk, a magnetic tape, or a signal encoding the process steps, and then stored in the storage device 630 in a compressed, uncompiled, and/or encrypted format. In alternative embodiments, hard-wired circuitry may be used in place of, or in combination with, processor-executable process steps for implementation of processes according to embodiments of the present invention. Thus, embodiments of the present invention are not limited to any specific combination of hardware and software. The programs 612, 614 may furthermore include other program elements, such as an operating system, a database management system, and/or device drivers used by the processor 610 to interface with peripheral devices.

As used herein, information may be "received" or "retrieved" by or "transmitted" to, for example: (i) the Respiration Rate Platform 600 from another device; or (ii) a software application or module within the Respiration Rate Platform 600 from another software application, module, or any other source.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The flowchart and block diagrams in the Figures illustrate the architecture, functionality, and operation of possible implementations of systems, methods and computer programs products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, a respiration module, a respiration rate analysis module, and an alert module. The method steps can then be carried out using the distinct software modules and/or sub-modules of the system, as described above, executing on one or more hardware processors 610 (FIG. 6). Further, a computer program product can include a computer-readable storage medium with code adapted to be implemented to carry out one or more method steps described herein, including the provision of the system with the distinct software modules.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
providing a plurality of sensors proximate a subject, wherein each sensor includes a plurality of antennas, and wherein each sensor operates on a plurality of frequency channels;
receiving, at a respiration module, a signal associated with each antenna for each of the plurality of frequency channels; and
calculating a respiration rate of the subject based on the received signal associated with each antenna for each of the plurality of frequency channels.

2. The method of claim 1, further comprising:
calculating a quality metric for each received signal, wherein the quality metric is one of a Received Signal Strength (RSS), a Link Quality Indicator (LQI), and Bit Error Rate (BER).

3. The method of claim 2, further comprising:
determining a power spectral density (PSD) based on the quality metric for each received signal; and
calculating a respiration rate of the subject based on PSD.

4. The method of claim 2, further comprising:
calculating a Received Signal Strength (RSS) for each received signal with the respiration module;
determining a power spectral density (PSD) based on the RSS for each received signal; and
calculating a respiration rate of the subject based on the PSD.

5. The method of claim 4, further comprising:
calculating a time series of RSS change for a time window to capture a periodic change of RSS.

6. The method of claim 5, wherein calculating a time series of RSS change further comprises:
determining an average RSS for the plurality of received signals for the time window.

7. The method of claim 6, further comprising:
subtracting the average RSS for the plurality of received signals during the time window from each of the plurality of received RSS signals during the time window.

8. The method of claim 4, wherein calculating a respiration rate of the subject based on the PSD further comprises calculating the frequency associated with a maximum PSD, via:

$$\hat{f} = \underset{f_{min} \leq f \leq f_{max}}{\operatorname{argmax}} \sum_{l=1}^{L} \sum_{c=1}^{C} g(y_{c,l,T}) \quad (1)$$

where $\hat{f}$ is the estimate of respiration rate/frequency, arg max $_{f_{min} \leq f \leq f_{max}}$ is the operator to find the maximum PSD value, L is the number of links, C is the number of frequency channels, $y_{c,l,T}$ is a time series of RSS changes collected from link l on Channel c during a time period of length T, and g represents a particular PSD estimator.

9. The method of claim 8, wherein the PSD estimator is one of a periodogram estimator, a Welch estimator and a Bartlett's method estimator.

10. The method of claim 9, wherein determining a PSD further comprises:
applying a maximum likelihood estimation (MLE) method used by the periodogram estimator to each of the plurality of received RSS in the time window to calculate the PSD for each received RSS in the RSS time window.

11. The method of claim 10, wherein applying the MLE method to calculate the respiration rate of the subject comprises:

$$\hat{f} = \underset{f_{min} \leq f \leq f_{max}}{\operatorname{argmax}} \sum_{l=1}^{L} \sum_{c=1}^{C} \left| \sum_{t=i-m+1}^{i} y_{c,l,t} e^{-j2\pi f T_s t} \right|^2,$$

wherein l is a link, c is a frequency channel, t is time, m is the length of the window, L is the number of links, C is the number of frequency channels, i is the current time index, $y_{c,l,t}$ is the RSSI change for the time window, $j=\sqrt{-1}$ and $T_s$ is the sampling period.

12. The method of claim 3, wherein calculating the respiration rate of the subject based on the PSD further comprises:
determining a maximum PSD from the plurality of calculated PSDs for each received signal quality metric and a frequency associated with the maximum PSD.

13. The method of claim 1, further comprising:
storing the calculated respiration rate.

14. The method of claim 1, further comprising:
comparing calculated respiration rate to a threshold to analyze the patient; and
generating at least one of an audio output, a visual output, an alert message, or combinations thereof, upon determining that the calculated respiration rate is outside a corresponding threshold based on the comparison.

15. The method of claim 1, wherein the plurality of sensors do not touch the subject.

16. A system comprising:
a plurality of sensors, positioned proximate a subject, wherein each sensor includes a plurality of antennas, and wherein each sensor operates on a plurality of frequency channels;
a respiration module operative to:
receive a signal associated with each antenna for each of the plurality of frequency channels; and
calculate a respiration rate of the subject based on the received signal associated with each antenna for each of the plurality of frequency channels.

17. The system of claim 16, wherein the respiration module is further operative to:
calculate a quality metric for each received signal, wherein the quality metric is one of a Received Signal Strength (RSS), a Link Quality Indicator (LQI), and Bit Error Rate (BER).

18. The system of claim 17, wherein the respiration module is further operative to:
calculate a Received Signal Strength (RSS) for each received signal;

determine a power spectral density (PSD) based on the RSS for each received signal; and calculate a respiration rate of the subject based on the PSD.

19. The system of claim 18, wherein the respiration module is further operative to:

calculate a time series of RSS change for a time window to capture a periodic change of RSS.

20. The system of claim 19, wherein to calculate a time series of RSS change, the respiration module is further operative to:

determine an average RSS for the plurality of received signals for the time window; and subtract the average RSS for the plurality of received signals during the time window from each of the plurality of received RSS signals during the time window.

21. The system of claim 18, wherein calculating a respiration rate of the subject based on the PSD further comprises calculating a frequency associated with a maximum PSD via:

$$\hat{f} = \underset{f_{min} \leq f \leq f_{max}}{\mathrm{argmax}} \sum_{l=1}^{L} \sum_{c=1}^{C} g(y_{c,l,T}) \quad (1)$$

where $\hat{f}$ is the estimate of respiration rate/frequency, arg max $f_{min} \leq f \leq f_{max}$ is the operator to find the maximum PSD value, L is the number of links, C is the number of frequency channels, $y_{c,l,T}$ is the RSSI time series collected from link l on Channel c during a time period of length T, and g represents a particular PSD estimator.

22. The system of claim 21, wherein the PSD estimator is one of a periodogram estimator, a Welch estimator and a Bartlett's method estimator.

23. The system of claim 22, wherein the respiration module is operative to apply a maximum likelihood estimation (MLE) method used by the periodogram estimator to each of the plurality of received RSS in the time window to calculate the PSD for each received RSS in the RSS time window.

24. The system of claim 23, wherein the application of the MLE method comprises:

$$\hat{f} = \underset{f_{min} \leq f \leq f_{max}}{\mathrm{argmax}} \sum_{l=1}^{L} \sum_{c=1}^{C} \left| \sum_{t=i-m+1}^{i} y_{c,l,t} e^{-j2\pi f T_s t} \right|^2 ,$$

wherein l is a link, c is a frequency channel, t is time, m is the length of the window, L is the number of links, C is the number of frequency channels, i is the current time index, $y_{c,l,t}$ is the RSSI change for the time window, $j=\sqrt{-1}$ and $T_s$ is the sampling period.

25. The system of claim 24, wherein a frequency associated with a maximum PSD from the plurality of calculated PSDs is the respiration rate of the subject.

26. The system of claim 16, further comprising:

a respiration rate storage module operative to store the calculated respiration rate.

27. The system of claim 16, further comprising:

a respiration rate analysis module operative to:

compare the calculated respiration rate to a threshold to analyze the patient; and generate at least one of an audio output, a visual output, an alert message, or combinations thereof, upon determining that the calculated respiration rate is outside a corresponding threshold based on the comparison.

28. The system of claim 16, wherein the plurality of sensors do not touch the subject.

* * * * *